US010974168B2

(12) United States Patent
Conradie et al.

(10) Patent No.: US 10,974,168 B2
(45) Date of Patent: *Apr. 13, 2021

(54) MATERIALS AND METHODS FOR THE SELECTIVE RECOVERY OF MONOVALENT PRODUCTS FROM AQUEOUS SOLUTIONS USING CONTINUOUS ION EXCHANGE

(71) Applicant: INV NYLON CHEMICALS AMERICAS, LLC, Wilmington, DE (US)

(72) Inventors: Alex Conradie, Eaglescliffe (GB); Gary J. Smith, Wilton (GB); Paul S. Pearlman, Thornton, PA (US); Gregory S. Kirby, Avondale, PA (US); Mariusz Kamionka, Eaglescliffe (GB)

(73) Assignee: INV Nylon Chemicals Americas, LLC, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 15/491,018

(22) Filed: Apr. 19, 2017

(65) Prior Publication Data

US 2017/0349535 A1    Dec. 7, 2017

Related U.S. Application Data

(63) Continuation of application No. 15/094,791, filed on Apr. 8, 2016, now abandoned.

(60) Provisional application No. 62/144,858, filed on Apr. 8, 2015.

(51) Int. Cl.
| | | |
|---|---|---|
| C07C 51/47 | (2006.01) |
| B01D 15/36 | (2006.01) |
| C07C 227/40 | (2006.01) |
| C07C 67/58 | (2006.01) |
| B01D 15/20 | (2006.01) |
| B01D 15/18 | (2006.01) |
| C07C 53/126 | (2006.01) |
| C07C 229/06 | (2006.01) |

(52) U.S. Cl.
CPC ....... B01D 15/362 (2013.01); B01D 15/1892 (2013.01); B01D 15/20 (2013.01); B01D 15/361 (2013.01); C07C 51/47 (2013.01); C07C 53/126 (2013.01); C07C 67/58 (2013.01); C07C 227/40 (2013.01); C07C 229/06 (2013.01)

(58) Field of Classification Search
CPC .. B01D 15/1892; B01D 15/20; B01D 15/361; B01D 15/362; C07C 67/58; C07C 227/40; C07C 229/06; C07C 51/47; C07C 53/126

See application file for complete search history.

(56) References Cited

U.S. PATENT DOCUMENTS

| | | | |
|---|---|---|---|
| 2,839,548 A * | 6/1958 | Berther | B01J 47/04 562/553 |
| 2,985,589 A | 5/1961 | Broughton et al. | |
| 3,017,435 A | 1/1962 | Coffman et al. | |
| 3,069,465 A | 12/1962 | Monet | |
| 3,393,233 A | 7/1968 | Richter | |
| 3,578,432 A * | 5/1971 | Stiles | A01C 23/042 210/687 |
| 3,696,107 A | 10/1972 | Neuzil | |
| 3,706,812 A | 12/1972 | Derosset et al. | |
| 3,761,533 A | 9/1973 | Otani et al. | |
| 4,263,145 A | 4/1981 | Wirth, Jr. | |
| 4,323,702 A | 4/1982 | Kawabata et al. | |
| 4,333,740 A | 6/1982 | Priegnitz | |
| 4,461,649 A | 1/1984 | Neuzil et al. | |
| 4,483,980 A | 11/1984 | Neuzil et al. | |
| 4,584,400 A | 4/1986 | Ohtani et al. | |
| 4,663,048 A | 5/1987 | Tanaka et al. | |
| 4,720,579 A | 1/1988 | Kulprathipanja | |
| 4,764,276 A | 8/1988 | Berry et al. | |
| 4,851,573 A | 7/1989 | Kulprathipanja et al. | |
| 4,851,574 A | 7/1989 | Kulprathipanja et al. | |
| 5,026,482 A | 6/1991 | Sircar | |
| 5,069,883 A | 12/1991 | Matonte | |
| 5,071,560 A | 12/1991 | McCulloch et al. | |
| 5,279,744 A | 1/1994 | Itoh et al. | |
| 5,405,992 A | 4/1995 | Funk et al. | |
| 5,663,424 A | 9/1997 | Knofel et al. | |
| 5,684,190 A | 11/1997 | Fechter et al. | |
| 5,759,406 A | 5/1998 | Nakazawa et al. | |
| 5,751,406 A | 6/1998 | Phelps et al. | |
| 5,779,814 A | 7/1998 | Fellers, Sr. et al. | |
| 6,099,654 A | 8/2000 | Kaneko et al. | |
| 6,146,534 A | 11/2000 | Grendze et al. | |
| 6,153,791 A | 11/2000 | Moore | |
| 6,284,904 B1 | 9/2001 | Ponnampalam | |
| 6,462,221 B1 | 10/2002 | Gabriel et al. | |
| 6,476,239 B1 | 11/2002 | Arumugam et al. | |
| 6,518,454 B1 | 2/2003 | Arumugam et al. | |
| 6,872,314 B2 | 3/2005 | Boyd et al. | |
| 6,979,402 B1 | 12/2005 | Sprague et al. | |

(Continued)

FOREIGN PATENT DOCUMENTS

| | | |
|---|---|---|
| CA | 2404442 | 10/2001 |
| CN | 101823928 A | 9/2010 |
| CN | 102206167 | 10/2011 |
| CN | 106367326 | 2/2017 |
| CN | 108276292 | 7/2018 |

(Continued)

OTHER PUBLICATIONS

In Gonzalez-Pradas et al. (Removal of Aromatic Amines from Aqueous Solution by Activated Sepiolite, J. Chem. Tech. Biotechnol. 1990, 47, 15- 22) (Year: 1990).*

(Continued)

*Primary Examiner* — Jafar F Parsa
*Assistant Examiner* — Blaine G Doletski

(57) ABSTRACT

This document describes a process for the high purity and high concentration recovery of monovalent products via continuous ion exchange from aqueous solution for further down-stream purification.

8 Claims, 2 Drawing Sheets

(56) References Cited

U.S. PATENT DOCUMENTS

| | | | |
|---|---|---|---|
| 7,166,460 | B2 | 1/2007 | Wilkins et al. |
| 7,241,918 | B1 | 7/2007 | Kulprathipanja |
| 7,820,869 | B2 | 10/2010 | Priegnitz et al. |
| 8,729,298 | B2 | 5/2014 | Zang et al. |
| 9,061,267 | B2 | 6/2015 | Gottschall et al. |
| 9,233,906 | B2 | 1/2016 | Gerberding et al. |
| 9,315,443 | B2 | 4/2016 | Erhardt et al. |
| 9,878,321 | B2 | 1/2018 | Kamionka et al. |
| 10,265,642 | B2 | 4/2019 | Smith et al. |
| 10,343,084 | B2 | 7/2019 | Pearlman et al. |
| 2002/0035269 | A1 | 3/2002 | Soper et al. |
| 2003/0094416 | A1 | 5/2003 | Heikkila et al. |
| 2006/0058555 | A1 | 3/2006 | Ostermaier |
| 2007/0213415 | A1 | 9/2007 | Sarlis |
| 2009/0036709 | A1* | 2/2009 | Okada .......... C07C 229/22 562/567 |
| 2009/0326308 | A1 | 12/2009 | Kulprathipanja et al. |
| 2010/0108610 | A1 | 5/2010 | Godhwani et al. |
| 2010/0292429 | A1 | 11/2010 | Volkert et al. |
| 2011/0004018 | A1 | 1/2011 | Ito et al. |
| 2011/0160483 | A1 | 6/2011 | Rezkallah |
| 2012/0289742 | A1 | 11/2012 | Gerberding et al. |
| 2013/0030146 | A1* | 1/2013 | Guit .......... C07D 201/08 528/323 |
| 2013/0183728 | A1 | 7/2013 | Botes et al. |
| 2013/0210090 | A1 | 8/2013 | Pearlman et al. |
| 2013/0217081 | A1 | 8/2013 | Pearlman et al. |
| 2013/0224807 | A1 | 8/2013 | Pearlman et al. |
| 2014/0046023 | A1 | 2/2014 | Gottschall et al. |
| 2014/0051868 | A1 | 2/2014 | Sokolov et al. |
| 2014/0051888 | A1 | 2/2014 | Dubay et al. |
| 2014/0076805 | A1 | 3/2014 | Massingill |
| 2014/0186902 | A1 | 7/2014 | Botes et al. |
| 2014/0193865 | A1 | 7/2014 | Botes et al. |
| 2014/0199737 | A1 | 7/2014 | Botes et al. |
| 2014/0242655 | A1 | 8/2014 | Pearlman et al. |
| 2014/0248673 | A1 | 9/2014 | Botes et al. |
| 2015/0004660 | A1 | 1/2015 | Pearlman et al. |
| 2016/0159723 | A1 | 6/2016 | Smith et al. |
| 2016/0289165 | A1 | 10/2016 | Murata et al. |
| 2016/0296926 | A1 | 10/2016 | Kamionka et al. |
| 2016/0297746 | A1 | 10/2016 | Smith et al. |
| 2016/0297747 | A1 | 10/2016 | Conradie |
| 2016/0326112 | A1* | 11/2016 | Brichant .......... C07D 209/20 |
| 2017/0349535 | A1 | 12/2017 | Conradie |
| 2017/0369913 | A1 | 12/2017 | Suominen et al. |
| 2018/0023103 | A1 | 1/2018 | Foster et al. |
| 2020/0108331 | A1 | 4/2020 | Smith et al. |

FOREIGN PATENT DOCUMENTS

| | | |
|---|---|---|
| EP | 0324210 | 10/1990 |
| EP | 0415821 | 3/1991 |
| EP | 1 106 602 A1 | 6/2001 |
| EP | 2345632 | 7/2011 |
| EP | 2591773 | 5/2013 |
| EP | 2591778 | 5/2013 |
| FR | 2103302 | 4/1972 |
| FR | 2651148 | 3/1991 |
| FR | 2651149 | 3/1991 |
| WO | WO 90/08730 | 8/1990 |
| WO | WO 2013/005046 | 1/2013 |
| WO | WO 2014/113999 | 7/2014 |
| WO | 2016/164748 A1 | 10/2016 |
| WO | WO 2016/106367 | 10/2016 |
| WO | WO 2016/164748 | 10/2016 |
| WO | WO 2016/164767 | 10/2016 |
| WO | WO 2016/164798 | 10/2016 |

OTHER PUBLICATIONS

Gao et al. (Separation and Purification of γ-Aminobutyric Acid from Fermentation Broth by Flocculation and Chromatographic Methodologies, J. Agric. Food Chem. 2013, 61, 1914-1919). (Year: 2013).*

Amberlite (Year: 2008).*

Aminocaproic acid (published Mar. 2006) (Year: 2006).*

Walker et al. (Quantitative methods for amino acid analysis in biological fluids, Ann Clin Biochem; 32: 28-57 Published 1995) (Year: 1985).*

International Preliminary Report on Patentability issued in International Application No. PCT/US2016/026678, dated Oct. 19, 2017, 7 pages.

U.S. Non-Final Office Action issued in copending U.S. Appl. No. 15/094,791, filed Apr. 8, 2016, dated Oct. 25, 2016, 10 pages.

Kirk-Othmer, Encyclopedia of Chemical Technology, Fourth Edition, vol. 2, pp. 513-516 (1992).

Jansen, M.L. et al., "Effect of pH and Concentration on Column Dynamics of Weak Electrolyte Ion Exchange," AICHE Journal, vol. 42, No. 7, pp. 1925-1937 (1996).

Helfferich, F.G., "Ion Exchange Equilibria of Amino Acids on Strong-Acid Resins: Theory," Reactive Polymers, vol. 12, pp. 95-100 (1990).

International Search Report and Written Opinion for International Application No. PCT/US2016/026678, dated Jun. 29, 2016, from the International Searching Authority, European Patent Office (12 pages).

Anon, "Amine recovery using continuous ion-exchange" Research Disclosure, vol. 383, 1996, p. 206-.

Buhlert, "Construction and development of a new single-column simulated moving bed system on the laboratory scale" Journal of Chromatography A, 1216 (2009), p. 8778-8786.

ChEBI:59758-gamma-amino fatty acid definition, p. 1-2, last modified on Nov. 7, 2016, downloaded from http://www.ebi.ac.uk/chebi/searchId.do?chebild=59758.

Fritz. "Ion Chromatography" Analytical Chemistry, vol. 59, No. 4, 1987, p. 335A-344A.

International Preliminary Report on Patentability issued in International Application No. PCT/US2016/026712, dated Oct. 19, 2017, 10 pages.

International Search Report and Written Opinion for PCT/US2016/026712, issued from European Patent Office on Jun. 21, 2016 (15 pages).

International Search Report and Written Opinion for PCT/US2016/026754, issued from European Patent Office on Jun. 17, 2016 (13 pages)—11 pages.

International Preliminary Report on Patentability issued in International Application No. PCT/US2016/026754, dated Oct. 19, 2017 (10 pages).

International Search Report and Written Opinion for International Application No. PCT/US2019/051401, dated Dec. 11, 2019, (12 pages).

Jansen ML et al "Effect of pH and Concentration on Column Dynamics of Weak electrolyte Ion Exchange" AICHE Journal vol. 42 No. 7, (1996) pp. 1925-1937.

Latterell "Separation of Amines by Ligand Exchange. Part II" Analytica Chimica Acta, 32, 1965, p. 101-109.

Membrane Filtration Processes Technical Bulletin from TRISEP, p. 1-2, dated Jun. 9, 2016, downloaded from https://static1.squarespace.com/static/54e2b7aee4b0902efd671f90/t/580ff23b2e69cf6ad153bd42/1477440060214/TB-025+Membrane+Filtration+Processes+−+Dead-End+vs.+Cross-Flow+RevA.pdf.

Non Final Rejection received in U.S. Appl. No. 15/094,770, filed Apr. 8, 2016, dated Mar. 13, 2018, 43 pages.

Non-final office action received for U.S. Appl. No. 15/847,854 dated Jul. 14, 2020, 18 pages.

Notice of Allowance received in U.S. Appl. No. 15/094,770, filed Apr. 8, 2016, dated Nov. 30, 2016, 4 pages.

Notice of Allowance received in U.S. Appl. No. 15/094,770, filed Apr. 8, 2016, dated Oct. 28, 2016, 7 pages were filed.

Notice of Allowance received in U.S. Appl. No. 15/094,770, filed Apr. 8, 2016, dated Jan. 3, 2019, 15 pages.

Simulated Moving Bed wikipedia page, last edited May 5, 2017, p. 1-3, downloaded from https://en.wikipedia.org/wiki/Simulated_moving_bed.

(56) References Cited

OTHER PUBLICATIONS

Van Walsem, H.J., "Simulated Moving Bed in the Production of Lysine", Journal of Biotechnology vol. 59, (1997), pp. 127-132.
U.S. Non-Final Office Action issued in U.S. Appl. No. 15/094,770, filed Apr. 8, 2016, dated Jun. 15, 2017, 36 pages.
U.S. Non-Final Office Action issued in U.S Appl. No. 15/094,930, filed Apr. 8, 2016 dated Jun. 2, 2017, 12 pages.
U.S. Notice of Allowance mailed in U.S. Appl. No. 15/094,930, filed Apr. 8, 2016 dated Sep. 21, 2017, 7 pages.
U.S. Appl. No. 62/144,884, filed Apr. 18, 2015, 18 pages.
Final Office Action received for U.S. Appl. No. 16/572,899, dated Feb. 24, 2021, 14 pages.

\* cited by examiner

MATERIALS AND METHODS FOR THE SELECTIVE RECOVERY OF MONOVALENT PRODUCTS FROM AQUEOUS SOLUTIONS USING CONTINUOUS ION EXCHANGE

This application is a continuation of application Ser. No. 15/094,791, filed Apr. 8, 2016, and claims priority to U.S. provisional application No. 62/144,858, filed on Apr. 8, 2015, all of which is herein incorporated by reference in its entirety.

TECHNICAL FIELD

The present disclosure relates to methods for the selective recovery of a monovalent product from an aqueous solution using continuous ion exchange. For example, using a proton buffer zone, the method and materials provide for high adsorption loadings and high purity monovalent product. An intermediate product stream is produced for further purification, lowering the cost of the overall downstream processing.

SUMMARY

Monovalent products, i.e. molecules capable of carrying a valence state of one, require high concentration recovery from aqueous solutions, preferably at high purity, for further purification. The Nylon-6 monomer, 6-aminohexanoic acid, is of industrial relevance. The monomer 6-aminohexanoate is largely monovalent at pH ~2 and largely neutrally charged at pH ~7. The monomer 6-aminohexanoate may be produced via fermentation into an aqueous medium, which includes inorganic ionic species and other organic by-products, e.g. amino acids, as competitive species in adsorption processes such as ion exchange. Such monovalent by-products compete for adsorption sites at a pH ~2, resulting in a lower purity, high concentration, intermediate stream for purification. Recovery of monovalent 6-aminohexanoate at pH ~4 allows rejection of e.g. monovalent amino acid by-products from the ion exchange resin producing a high purity product, but given that a large fraction of the 6-aminohexanoate is neutrally charged, this results in a lower concentration of the intermediate stream for further purification.

Many other monovalent products produced into an aqueous medium require high purity and high concentration recovery prior to further economical purification. Such monovalent products include, but are not limited to, (1) fatty acids such as octanoic acid, (2) monoamines such as 4-aminobutyrate, 5-aminopentanoate, 6-aminohexanoate and 7-aminoheptanoate and (3) amino acids such as L-valine. Accordingly, against this background, it is clear that there is a need for methods underpinning the economic recovery of such monovalent products from aqueous solutions.

Recovery methods for purification of monovalent products can be implemented by a variety of different separation techniques. A non-limiting example includes optimizing the binding capacity of the charged compound via ion exchange. Ion exchange may involve at least one stage of adsorption, elution, and regeneration and in some applications, may include several regeneration and washing phases.

"Batch mode" involves applying a mixture to a single column and applying various eluents in succession to improve adsorption of the target compound to the ion exchange resin. After the adsorption step, the ion exchange resin can be regenerated with the appropriate eluent to repeat the process in a cyclical manner that does not attain steady state. Batch mode systems may be simple to use but can be impractical for large-scale industrial processes.

Continuous ion exchange may allow for simultaneous adsorption and regeneration steps and thus, be more efficient since there is an automated, continuous staging of the recovery process that attains steady state operation. And, given the trade-off between producing a high purity product at high concentration without significant recovery losses, continuous ion exchange offers an alternative approach achieving both aims for monovalent products.

Accordingly, the present disclosure relates to continuous ion exchange processes that allow high purity and high concentration recovery of monovalent products.

In at least one aspect, the disclosure relates to methods of recovering monovalent products at high purity and high concentration from an aqueous solution via continuous ion exchange using either cationic and/or anionic ion exchange adsorbents.

In one aspect, the present disclosure describes methods for recovering a monovalent product from an aqueous solution. For instance, in at least one embodiment, the operation includes feeding an unclarified or clarified solution to the continuous ion exchange unit operation and adsorbing the monovalent product at a pH of approximately the negative logarithm of the first acid dissociation constant, $pK_{a1}$. In one aspect, the methods include charging the columns cycling into the Proton Buffer Zone with protons that buffer the Dilute Adsorption Zone towards a pH of approximately the negative logarithm of the first acid dissociation constant, $pK_{a1}$. In another aspect, the present disclosure relates to the recovery of the monovalent product via elution from the ion exchange adsorbent using a high monovalent ionic concentration eluent, such as a solution comprising one or more compounds chosen from ammonia, ammonium carbonate, and ammonium bicarbonate. As a non-limiting example, the high monovalent ionic concentration eluent may be a concentrated ammonia solution (for example, 5-10% (w/w) of ammonia solution), a concentrated ammonium carbonate solution (for example, 1-2M of ammonium carbonate solution), a concentrated ammonium bicarbonate solution (for example, 1-2M of ammonium bicarbonate solution), or a solution mixture comprising two or more compounds chosen from ammonium carbonate, ammonium bicarbonate, and ammonia.

In at least one other aspect, the present disclosure describes an apparatus comprising a continuous ion exchange carousel comprised of a number of columns grouped into the zones described above for recovery of the monovalent product. The apparatus may comprise, for example, at least one Adsorption Zone, at least one Elution Zone, and at least one Proton Buffer Zone. In other embodiments, the apparatus may comprise at least one additional zone, for example, a Dilute Adsorption Zone, an Adsorption Wash Zone, a Back-Wash Zone, an Elution Wash Zone, and a Proton Buffer Wash Zone. In at least one embodiment, the apparatus comprises (1) a Dilute Adsorption Zone, (2) an Adsorption Zone, (3) an Adsorption Wash Zone, (4) a Back-Wash Zone, (5) an Elution Zone, (6) an Elution Wash Zone, (7) a Proton Buffer Zone and (8) a Proton Buffer Wash Zone.

Unless otherwise defined, all technical and scientific terms used herein have the same meaning as commonly understood by one of ordinary skill in the art to which this disclosure pertains. Although methods and materials similar or equivalent to those described herein can be used to practice the disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the present disclosure are set forth in the accompanying drawings and the description below. Other features, objects, and advantages of the present disclosure will be apparent from the description and drawings, and from the claims. The word "comprising" in the claims may be replaced by "consisting essentially of" or with "consisting of," according to standard practice in patent law.

DETAILED DESCRIPTION OF CERTAIN ASPECTS

Figure 1:
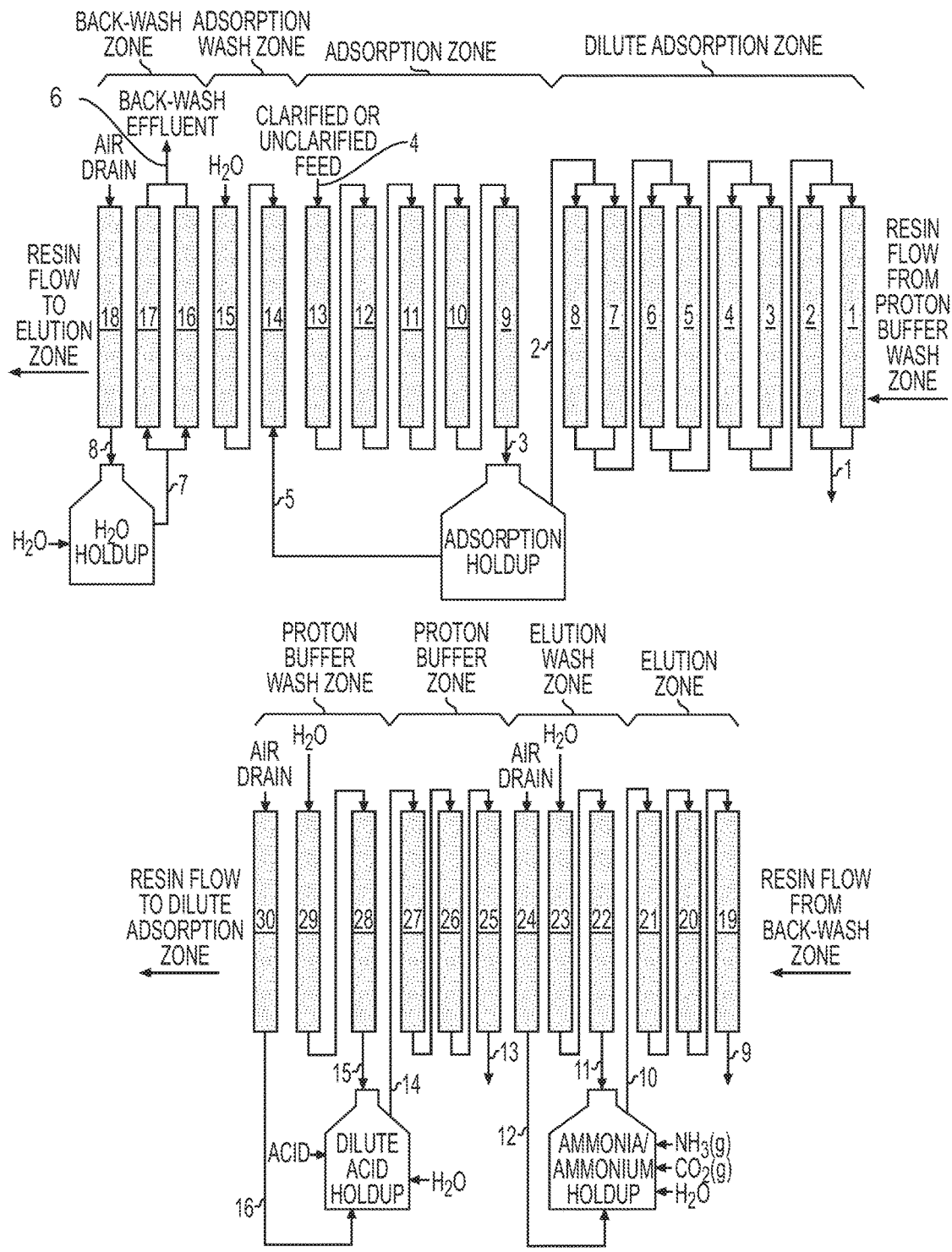
FIG. 1 is a schematic of an exemplary continuous ion exchange unit operation leading to the high purity and high concentration recovery of cationic monovalent products prior to further purification.

Before the present embodiments are described, it is to be understood that the present disclosure is not limited to the particular apparatus, adsorbents, zones, methodologies or protocols described, as these may vary. It is also to be understood that the terminology used in the description is for the purpose of describing the particular versions or embodiments only, and is not intended to limit the scope of the present disclosure.

In general, the present disclosure provides for continuous ion exchange methods for recovery of a monovalent product and an apparatus divided into a number of operating zones for production of a monovalent product for further purification.

According to the present disclosure, examples of monovalent products include, but are not limited to amino acids such as L-valine; fatty acids such as octanoic acid and monoamines such as 5-aminopentanoate, 6-aminohexanoate, 7-aminoheptanoate.

The term "monovalent" is used herein to denote a charged specie having a maximum valence of one, either 1+ or 1− valence.

As used herein, the terms "unclarified" refers to a solution containing solid particulates such as cells or precipitates and "clarified" solutions are understood to mean a solution from which solid particulates have been removed.

According to the present disclosure, "adsorption zone" is understood to mean a stage in the recovery method where the process stream containing the monovalent product to be recovered is added to a particular adsorbent resin and the monovalent product adsorbs to the adsorbent resin.

According to the present disclosure, "elution zone" is understood to mean a stage in the recovery method where the monovalent product adsorbed to the adsorbent resin is desorbed into the liquid phase.

According to the present disclosure, "proton buffer zone" is understood to mean a stage in the recovery method where a fraction of the adsorbent's active sites are charged with protons to provide buffering capacity in the dilute adsorption zone.

The terms "about" and "approximately," when used in connection with a specific value, means that acceptable deviations from that value are also encompassed but still provide substantially the same function as the specific value.

Accordingly, the presently defined methods provide for separation of monovalent products from aqueous solutions comprising monovalent products of interest and other impurities based on their varying affinities for the adsorbent resins. The monovalent products of interest may be retained by the adsorbent phase resin with the impurities passed through to waste. The aqueous solutions are passed through a series of columns comprising resins separated into adjacent zones, for example, rotating or stationary columns passed through the various zone via a rotating valve. Each zone comprises at least one column, but in at least one embodiment, may comprise multiple columns, for example, two or three columns.

In at least one embodiment, the methods comprise at least three zones, for example, an absorption zone, an elution zone, and a proton buffer zone. In other embodiments, the methods may comprise at least six zones, at least seven zones, or at least eight zones for recovery of the monovalent products of interest. In at least one embodiment, the methods comprise at least eight zones: dilute adsorption zone, adsorption zone, adsorption wash zone, back-wash zone, elution zone, elution wash zone, proton buffer zone, and a proton buffer wash zone. Additional wash and regeneration zones may also be included depending upon the monovalent product to be extracted.

The monovalent products of interest are extracted from the culture broth while impurities are discharged to the waste treatment. According to the present disclosure, the purity on total dissolved solids of the extracted product is for example, greater than about 75%, for example about 85%. In at least one embodiment, the monovalent product, 6-aminohexanoate is obtained at a purity of at least about 75%.

The ion exchange resins are conventional, and can be weak or strong anionic or cationic resins, depending on the nature of the particular product to be extracted. In at least one embodiment, only one type of ion exchange resin is used but in another embodiment, various types of ion exchange resins are used.

In some embodiments, the method of recovering at least one monovalent product from an aqueous solution using continuous ion exchange comprising:

a. adsorbing at least one monovalent product on an ion exchange resin at a pH of approximately the negative logarithm of a first acid dissociation constant of the at least one monovalent product;

b. eluting the at least one monovalent product from the ion exchange resin; and c. charging adsorbent sites on the ion exchange resin with a sufficient amount of protons or proton donors to provide buffering capacity towards the pH of approximately the negative logarithm of the at least one monovalent product's first acid dissociation constant.

In some embodiments, the at least one monovalent product is chosen from fatty acids, monoamines, and amino acids. In some embodiments, the monoamines comprise at least one of 4-aminobutyrate, 5-aminopentanoate, 6-aminohexanoate, and 7-aminoheptanoate.

In some embodiments, the at least one monovalent product is eluted from the ion exchange resin with a solution comprising at least one compound chosen from ammonia, ammonium carbonate, and ammonium bicarbonate.

In some embodiments, the method disclosed herein comprises charging the adsorbent site on the ion exchange resin with an acidic solution. In some embodiments, the acidic solution comprises sulphuric acid.

In some embodiments, the method disclosed herein comprises charging the adsorbent sites on the ion exchange resin with an ammonium bicarbonate solution.

In some embodiments, the method further comprises at least one wash step after at least one of steps (a), (b), and (c). In yet some embodiments, the at least one wash step comprises washing the ion exchange resin with an aqueous solution.

Also provided disclosed herein is an apparatus for recovering at least one monovalent product from aqueous solutions comprising:
  a. an absorption zone to adsorb at least one monovalent product on an ion exchange resin at a pH of approximately the negative logarithm of a first acid dissociation constant of the at least one monovalent product;
  b. an elution zone to elute the at least one monovalent product from the ion exchange resin; and
  c. a proton buffer zone for charging adsorbent sites on the ion exchange resin with a sufficient amount of protons or proton donors to provide buffering capacity towards the pH of approximately the negative logarithm of the at least one monovalent product's first acid dissociation constant.

In some embodiments, the at least one monovalent product is chosen from fatty acids, monoamines, and amino acids.

In some embodiments, the monoamines comprise at least one of 4-aminobutyrate, 5-aminopentanoate, 6-aminohexanoate, and 7-aminoheptanoate.

In some embodiments, the elution zone comprises at least one eluent chosen from ammonia, ammonium carbonate, and ammonium bicarbonate.

In some embodiments, the proton buffer zone comprises an ammonium bicarbonate solution for charging the adsorbent sites on the ion exchange resin.

In some embodiments, the proton buffer zone comprises an acidic solution for charging the adsorbent site on the ion exchange resin.

In some embodiments, the acidic solution comprises sulphuric acid.

In some embodiments, the apparatus disclosed herein further comprising at least one wash step zone after at least one of zones (a), (b), and (c).

In some embodiments, the at least one wash step zone comprises an aqueous solution for washing the ion exchange resin.

Cationic Monovalent Continuous Ion Exchange Recovery

A clarified or unclarified aqueous solution is pH adjusted to approximately the $pK_{a1}$ for the target monovalent products and fed to the Adsorption Zone (see e.g., STREAM 4, FIG. 1), fed counter-current to the flow of the adsorbent phase. In at least one aspect, the adsorbent phase is a strongly- or weakly-cationic resin. The flow-through from the Adsorption Zone (see e.g., STREAM 3, FIG. 1) is combined with the flow-through from the Adsorption Wash Zone (see e.g., STREAM 5, FIG. 1) into an adsorption hold-up vessel, subsequently fed to the Dilute Adsorption Zone (see e.g., STREAM 2, FIG. 1). The Adsorption Zone and Dilute Adsorption Zone facilitate adsorption of the monovalent product in the monovalent state onto the adsorbent phase, competing for adsorption sites with other charged inorganic and organic species in the aqueous medium. The adsorbent flow rate is set to allow for minimal or zero break-through of the monovalent product into the adsorption effluent (see e.g., STREAM 1, FIG. 1), whilst allowing for flow through of inorganic and organic charged and uncharged/neutrally charged species to waste treatment.

The adsorbent and interstitial hold-up in the Adsorption Zone (see e.g., COL POS: 13, FIG. 1) moves into the Adsorption Wash Zone. Water fed into the Adsorption Wash Zone (see e.g., COL POS: 15, FIG. 1) flushes the interstitial hold-up from the Adsorption Zone into the adsorption hold-up vessel, ensuring that no monovalent product, held interstitially, is carried forward into the Back-wash Zone.

The Back-wash Zone fluidises the resin beds (see e.g., COL POS: 16 & 17, FIG. 1), providing for entrained particulate removal from the adsorbent beds (see e.g., STREAM 6, FIG. 1). An air drain (see e.g., COL POS: 18), recovers the interstitial water hold-up carried forward from the Back-wash Zone into the back-wash water hold-up vessel (see e.g., STREAM 8, FIG. 1).

The adsorbed monovalent product moves from the Back-wash Zone (see e.g., COL POS: 18, FIG. 1) into the Elution Zone (see e.g., COL POS: 19, FIG. 1). The Elution Zone is fed from a high concentration of ammonia (e.g., 5-10% (w/w)), ammonium carbonate (e.g., 1-2M), ammonium bicarbonate (e.g., 1-2M), or mixtures comprising two or more compounds chosen from ammonia, ammonium carbonate, and ammonium bicarbonate hold-up vessel (see e.g., STREAM 10, FIG. 1), eluting all monovalent product from the adsorbent. The eluate (see e.g., STREAM 9, FIG. 1) is fed to down-stream processing for further purification.

The regenerated resin moves from the Elution Zone (see e.g., COL POS: 21, FIG. 1) into the Elution Wash Zone (see e.g., COL POS: 22, FIG. 1). Water fed into the Elution Wash Zone (see e.g., COL POS: 23, FIG. 1) flushes interstitial ammonia, ammonium carbonate, ammonium bicarbonate, or mixtures thereof into the hold-up vessel (see e.g., STREAM 11, FIG. 1). The interstitial water is recovered via an air drain (see e.g., COL POS: 24, FIG. 1) into the concentrated ammonia, ammonium carbonate, ammonium bicarbonate, or mixtures thereof hold-up (see e.g., STREAM 12, FIG. 1).

The regenerated resin moves from the Elution Wash Zone (see e.g., COL POS: 24, FIG. 1) into the Proton Buffer Zone (see e.g., COL POS: 25, FIG. 1). The Proton Buffer Zone is fed from a dilute concentration acid hold-up vessel at a feed rate that adsorbs protons to a fraction of the adsorbent sites, thereby providing buffering capacity in the Dilute Adsorption Zone towards approximately the $pK_{a1}$ for the monovalent product. In one aspect of the disclosure, the acid may comprise sulphuric acid, for example an approximately 5% (w/w) sulphuric acid solution.

The proton charged adsorbent moves from the Proton Buffer Zone (see e.g., COL POS: 27, FIG. 1) into the Proton Buffer Wash Zone (see e.g., COL POS: 28, FIG. 1). An aqueous solvent such as water is fed into the Proton Buffer Wash Zone (see e.g., COL POS: 29, FIG. 1) flushes interstitial acid into the dilute acid hold-up vessel (see e.g., STREAM 15, FIG. 1). The interstitial water is recovered via an air drain (see e.g., COL POS: 30, FIG. 1) into the dilute acid hold-up (see e.g., STREAM 16, FIG. 1).

The adsorbent moves from the Proton Buffer Wash Zone (see e.g., COL POS: 30, FIG. 1) into the Dilute Adsorption Zone (see e.g., COL POS: 1, FIG. 1) and the adsorbent repeats the passage through the various continuous adsorption zones as described above.

Anionic Monovalent Continuous Ion Exchange Recovery

A clarified or unclarified aqueous solution is pH adjusted to approximately the $pK_{a1}$ for the target monovalent products and fed to the Adsorption Zone (see e.g., STREAM 4, FIG. 2), fed counter-current to the flow of the adsorbent phase. In at least one aspect, the adsorbent phase is a strongly- or weakly-anionic resin.

The flow-through from the Adsorption Zone (see e.g., STREAM 3, FIG. 2) is combined with the flow-through from the Adsorption Wash Zone (see e.g., STREAM 5, FIG. 2) into an adsorption hold-up vessel, subsequently fed to the Dilute Adsorption Zone (see e.g., STREAM 2, FIG. 2). The Adsorption Zone and Dilute Adsorption Zone facilitate adsorption of the monovalent product in the monovalent state onto the adsorbent phase, competing for adsorption sites with other charged inorganic and organic species in the aqueous medium. The adsorbent flow rate is set to allow for minimal or zero break-through of the monovalent product into the adsorption effluent (see e.g., STREAM 1, FIG. 2), whilst allowing for flow through of inorganic and organic charged and uncharged/neutrally charged species to waste treatment.

The adsorbent and interstitial hold-up in the Adsorption Zone (see e.g., COL POS: 15, FIG. 2) moves into the Adsorption Wash Zone. Water fed into the Adsorption Wash Zone (see e.g., COL POS: 18, FIG. 2) flushes the interstitial hold-up from the Adsorption Zone into the adsorption hold-up vessel, ensuring that no monovalent product, held interstitially, is carried forward into the Back-wash Zone.

Figure 2:
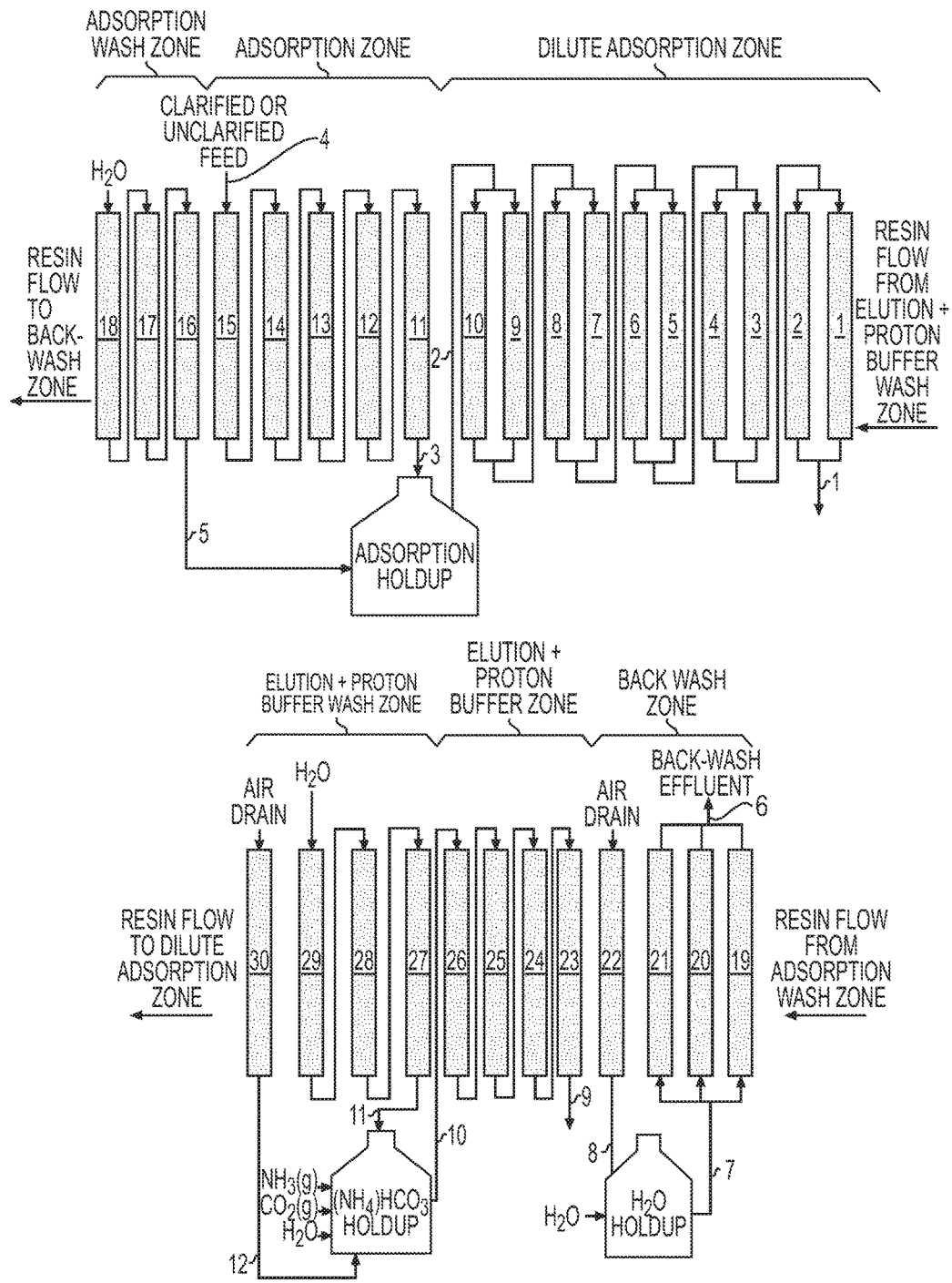
FIG. 2 is a schematic of an exemplary continuous ion exchange unit operation leading to the high purity and high concentration recovery of anionic monovalent products prior to further purification.

The Back-wash Zone fluidises the resin beds (see e.g., COL POS: 19 to 21, FIG. 2), providing for entrained particulate removal from the adsorbent beds (see e.g., STREAM 6, FIG. 2). An air drain (see e.g., COL POS: 22), recovers the interstitial water hold-up carried forward from the Back-wash Zone into the back-wash water hold-up vessel (see e.g., STREAM 8, FIG. 2).

The adsorbed monovalent product moves from the Back-wash Zone (see e.g., COL POS: 22, FIG. 2) into the Elution+Proton Buffer Zone (see e.g., COL POS: 23, FIG. 2). The Elution+Proton Buffer Zone is fed from a high concentration ammonium bicarbonate hold-up vessel (see e.g., STREAM 10, FIG. 2), eluting all monovalent product from the adsorbent. The eluate (see e.g., STREAM 9, FIG. 2) is fed to down-stream processing for further purification.

The regenerated resin moves from the Elution+Proton Buffer Zone (see e.g., COL POS: 26, FIG. 2) into the Elution+Proton Buffer Wash Zone (see e.g., COL POS: 27, FIG. 2). Water fed into the Elution+Proton Buffer Wash Zone (see e.g., COL POS: 29, FIG. 2) flushes interstitial ammonium bicarbonate into the hold-up vessel (see e.g., STREAM 11, FIG. 2). The interstitial water is recovered via an air drain (see e.g., COL POS: 30, FIG. 2) into the ammonium bicarbonate hold-up (see e.g., STREAM 12, FIG. 2).

The adsorbent moves from the Elution+Proton Buffer Wash Zone (see e.g., COL POS: 30, FIG. 2) into the Dilute Adsorption Zone (see e.g., COL POS: 1, FIG. 2) and the adsorbent repeats the passage through the various continuous adsorption zones as described above.

Another aspect of the present disclosure is to provide a bio-derived product, bio-based product, or fermentation-derived product, wherein said product is obtained from a process comprising the recovery methods disclosed herein.

Also another aspect of the present disclosure is to provide a bio-derived product, bio-based product, or fermentation-derived product, wherein said product is obtained from a process using the continuous ion exchange operation units disclosed herein.

In yet another aspect, the present disclosure relates to a bio-derived product, bio-based product or fermentation-derived product, wherein said product is obtained from processes disclosed herein and/or comprises:

i. a composition comprising at least one bio-derived, bio-based or fermentation-derived compound recovered from an operation system according FIG. 1 or FIG. 2 or any combination thereof, ii. a bio-derived, bio-based or fermentation-derived polymer comprising the bio-derived, bio-based or fermentation-derived composition or compound of i., or any combination thereof, iii. a bio-derived, bio-based or fermentation-derived resin comprising the bio-derived, bio-based or fermentation-derived compound or bio-derived, bio-based or fermentation-derived composition of i. or any combination thereof or the bio-derived, bio-based or fermentation-derived polymer of ii. or any combination thereof, iv. a molded substance obtained by molding the bio-derived, bio-based or fermentation-derived polymer of ii. or the bio-derived, bio-based or fermentation-derived resin of iii., or any combination thereof, v. a bio-derived, bio-based or fermentation-derived formulation comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., or bio-derived, bio-based or fermentation-derived molded substance of iv, or any combination thereof, or vi. a bio-derived, bio-based or fermentation-derived semi-solid or a non-semi-solid stream, comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., bio-derived, bio-based or fermentation-derived formulation of v., or bio-derived, bio-based or fermentation-derived molded substance of iv., or any combination thereof.

EXAMPLES

Example 1

Recovery of 6-Aminohexanoate from Fermentation Broth Using a Proton Buffer Zone in Continuous Ion Exchange A continuous ion exchange process as outlined in FIG. 1 may be set up by charging 30 columns interconnected via a multi-port rotating valve with a cationic exchange resin. The resin may be prepared to receive a fermentation broth feed by cycling all 30 columns through the continuous ion exchange zones, for example, as outlined in FIG. 1, thereby charging the active sites of the resin in the Adsorption Zone with ammonium ions, $NH_4^+$, and a fraction of buffering protons, $H^+$.

The Nylon-6 monomer, 6-aminohexanoate, can be produced via fermentation and excreted to the extracellular media. Unclarified fermentation broth containing 6-aminohexanoate as monovalent product may be pH adjusted to approximately the pKa1 of 6-aminohexanoic acid, 4.4. The pH adjusted broth may then be fed to the Adsorption Zone (see e.g., STREAM 4, FIG. 1), adsorbing the 6-aminohexanoate to the resin, consequently desorbing $NH_4^+$ and $H^+$ to the fluid phase.

The flow-through from the Adsorption Zone (see e.g., STREAM 3, FIG. 1) can be combined with the flow-through from the Adsorption Wash Zone (see e.g., STREAM 5, FIG. 1) into an adsorption hold-up vessel, subsequently fed to the Dilute Adsorption Zone (see e.g., STREAM 2, FIG. 1). The adsorbent flow rate may be set to allow for minimal breakthrough of the 6-aminohexanoate into the adsorption effluent (see e.g., STREAM 1, FIG. 1), whilst allowing for flow through of inorganic and organic charged and uncharged/neutrally charged species to waste treatment. The desorption of the protons charged to the resin in the Proton Buffer Zone, buffers the pH of the fluid phase such that the pH of STREAM 1 (FIG. 1) can be maintained approximately at the feed pH of 4.4.

The multi-port rotating valve moves the adsorbent and interstitial hold-up in the Adsorption Zone (see e.g., COL POS: 13, FIG. 1) into the Adsorption Wash Zone. Water is fed into the Adsorption Wash Zone (see e.g., COL POS: 15, FIG. 1) which may flush the interstitial hold-up from the Adsorption Zone into the adsorption hold-up vessel, ensuring that no 6-aminohexanoate, held interstitially, is carried forward into the Back-wash Zone.

The resin charged with 6-aminohexanoate moves via indexing of the multi-port rotating valve to the Back-wash Zone, where the resin beds (see e.g., COL POS: 16 & 17, FIG. 1) are fluidised, providing for entrained particulate removal from the adsorbent beds (see e.g., STREAM 6, FIG. 1). An air drain (see e.g., COL POS: 18) post the back-wash zone, recovers the interstitial water hold-up carried forward from the Back-wash Zone into the back-wash water hold-up vessel (see e.g., STREAM 8, FIG. 1).

The adsorbed 6-aminohexanoate moves via the indexing of the multi-port rotating valve from the Back-wash Zone (see e.g., COL POS: 18, FIG. 1) into the Elution Zone (see e.g., COL POS: 19, FIG. 1). The Elution Zone is fed, for instance, with an approximately 5% (w/w) ammonia solution, a 2 M ammonium bicarbonate or ammonium carbonate solution or a mixture of ammonia/ammonium carbonate/ammonium bicarbonate from an ammonia/ammonium carbonate/ammonium bicarbonate hold-up vessel (see e.g., STREAM 10, FIG. 1), eluting the adsorbed 6-aminohexanoate from the resin. The eluate (see e.g., STREAM 9, FIG. 1) may then be collected for analysis.

The regenerated resin moves via indexing of the multi-port rotating valve from the Elution Zone (see e.g., COL POS: 21, FIG. 1) into the Elution Wash Zone (see e.g., COL POS: 22, FIG. 1). Water is fed into the Elution Wash Zone (see e.g., COL POS: 23, FIG. 1), flushing interstitial ammonia/ammonium carbonate/ammonium bicarbonate into the concentrated ammonia/ammonium carbonate/ammonium bicarbonate hold-up vessel (see e.g., STREAM 11, FIG. 1). The interstitial water may then be recovered via an air drain (see e.g., COL POS: 24, FIG. 1) into the concentrated ammonia/ammonium bicarbonate/ammonium bicarbonate hold-up (see e.g., STREAM 12, FIG. 1).

The regenerated resin moves via the indexing of the multi-port rotating valve from the Elution Wash Zone (see e.g., COL POS: 24, FIG. 1) into the Proton Buffer Zone (see e.g., COL POS: 25, FIG. 1). The Proton Buffer Zone is fed, for instance, with an approximately 5% (w/w) sulphuric acid solution from a dilute concentration acid hold-up vessel at a feed rate that maintains the pH in STREAM 1 (FIG. 1) at the $pK_{a1}$ of approximately 4.4.

The proton charged adsorbent moves via the indexing of the multi-port rotating valve from the Proton Buffer Zone (see e.g., COL POS: 27, FIG. 1) into the Proton Buffer Wash Zone (see e.g., COL POS: 28, FIG. 1). Water is fed into the Proton Buffer Wash Zone (see e.g., COL POS: 29, FIG. 1), flushing interstitial acid into the dilute acid hold-up vessel (see e.g., STREAM 15, FIG. 1). The interstitial water may be recovered via an air drain (see e.g., COL POS: 30, FIG. 1) into the dilute acid hold-up (see e.g., STREAM 16, FIG. 1).

The adsorbent moves via the indexing of the multi-port rotating valve from the Proton Buffer Wash Zone (see e.g., COL POS: 30, FIG. 1) into the Dilute Adsorption Zone (see e.g., COL POS: 1, FIG. 1) and the adsorbent repeats the passage through the various zones as described above.

At steady state, the continuous ion exchange arrangement may recover approximately 98.5 [%](w/w) of the 6-aminohexanoate from the fermentation broth. The purity of the eluate on a total dissolved solids basis may be greater than approximately 75 [%](w/w) and the 6-aminohexanoate may be concentrated in the eluate to more than 1.5 fold that of the fermentation broth concentration.

Example 2

Recovery of Octanoate from Fermentation Broth Using a Proton Buffer Zone in Continuous Ion Exchange A continuous ion exchange process as outlined, for example in FIG. 2, may be set up, charging 30 columns interconnect via a multi-port rotating valve with an anionic exchange resin. The resin can be prepared to receive a fermentation broth feed by cycling all 30 columns through the continuous ion exchange zones outlined in FIG. 2, thereby charging the active sites of the resin in the Adsorption Zone with bicarbonate ions, $HCO_3^-$.

Octanoate may be produced via fermentation and excreted to the extracellular media. Unclarified fermentation broth containing octanoate as monovalent product can be pH adjusted to approximately the pKa1 of octanoic acid, 4.9. The pH adjusted broth may then be fed to the Adsorption Zone (see e.g., STREAM 4, FIG. 2), adsorbing the octanoate to the resin, consequently desorbing $HCO_3^-$ to the fluid phase.

The flow-through from the Adsorption Zone (see e.g., STREAM 3, FIG. 2) may be combined with the flow-through from the Adsorption Wash Zone (see e.g., STREAM 5, FIG. 2) into an adsorption hold-up vessel, subsequently fed to the Dilute Adsorption Zone (see e.g., STREAM 2, FIG. 2). The adsorbent flow rate may be allowed to set for minimal break-through of the octanoate into the adsorption effluent (see e.g., STREAM 1, FIG. 2), whilst allowing for flow through of inorganic and organic charged and uncharged/neutrally charged species to waste treatment. The desorption of the bicarbonates charged to the resin in the Elution+Proton Buffer Zone, may buffer the pH of the fluid phase such that the pH of STREAM 1 (FIG. 2) is maintained approximately at the feed pH of 4.9.

The multi-port rotating valve may move the adsorbent and interstitial hold-up in the Adsorption Zone (see e.g., COL POS: 15, FIG. 2) into the Adsorption Wash Zone. Water may be fed into the Adsorption Wash Zone (see e.g., COL POS: 18, FIG. 2) which flushes the interstitial hold-up from the Adsorption Zone into the adsorption hold-up vessel, ensuring that no octanoate, held interstitially, is carried forward into the Back-wash Zone.

The resin charged with octanoate may move via indexing of the multi-port rotating valve to the Back-wash Zone, where the resin beds (see e.g., COL POS: 19 to 21, FIG. 2) are fluidised, providing for entrained particulate removal from the adsorbent beds (see e.g., STREAM 6, FIG. 2). An air drain (see e.g., COL POS: 22) post the back-wash zone, recovers the interstitial water hold-up carried forward from the Back-wash Zone into the back-wash water hold-up vessel (see e.g., STREAM 8, FIG. 2).

The adsorbed octanoate moves via the indexing of the multi-port rotating valve from the Back-wash Zone (see e.g., COL POS: 22, FIG. 2) into the Elution Zone (see e.g., COL POS: 23, FIG. 2). The Elution+Proton Buffer Zone may be fed with a 2 M ammonium bicarbonate solution from a hold-up vessel (see e.g., STREAM 10, FIG. 2), eluting the adsorbed octanoate from the resin. The eluate (see e.g., STREAM 9, FIG. 2) may then be collected for analysis.

The regenerated resin moves via indexing of the multi-port rotating valve from the Elution+Proton Buffer Zone (see e.g., COL POS: 26, FIG. 2) into the Elution+Proton Buffer Wash Zone (see e.g., COL POS: 22, FIG. 1). Water is fed into the Elution Wash Zone (see e.g., COL POS: 23, FIG. 1), flushing interstitial ammonium bicarbonate into the concentrated ammonium bicarbonate hold-up vessel (see e.g., STREAM 11, FIG. 2). The interstitial water is recovered via an air drain (see e.g., COL POS: 30, FIG. 2) into the concentrated ammonium bicarbonate hold-up (see e.g., STREAM 12, FIG. 1).

The adsorbent moves via the indexing of the multi-port rotating valve from the Elution+Proton Buffer Wash Zone (see e.g., COL POS: 30, FIG. 2) into the Dilute Adsorption Zone (see e.g., COL POS: 1, FIG. 2) and the adsorbent repeats the passage through the various zones as described above.

At steady state, the continuous ion exchange arrangement may recover approximately 98.5% (w/w) of the octanoate from the fermentation broth. The purity of the eluate on a total dissolved solids basis may be greater than approximately 75% (w/w) and the octanoate may be concentrated in the eluate to more than 1.5 fold that of the fermentation broth concentration.

What is claimed is:

1. A method of recovering at least one monoamine from an aqueous solution using continuous ion exchange, comprising:

a) charging adsorbent sites on an ion exchange resin in at least two columns connected in series with a sufficient amount of protons or proton donors to provide buffering capacity at a pH of approximately $pK_{a1}$, wherein $K_{a1}$ is the first acid dissociation constant of the at least one monoamine; and b) adsorbing the at least one monoamine onto the charged ion exchange resin;

c) eluting the at least one monoamine from the ion exchange resin, wherein the at least one monoamine is not 4-aminobutyrate or 4-aminobutyric acid or a salt of either of the foregoing;

d) recovering the at least one monoamine under continuous operation at steady state.

2. The method of claim 1, wherein the at least one monoamine is chosen from 5-aminopentanoic acid, 6-aminohexanoic acid, and 7-aminoheptanoic acid, and salts thereof.

3. The method of claim 1, wherein the at least one monoamine is eluted from the ion exchange resin with a solution comprising at least one compound chosen from ammonia, ammonium carbonate, and ammonium bicarbonate.

4. The method of claim 1, comprising charging the adsorbent site on the ion exchange resin with an acidic solution.

5. The method of claim 4, wherein the acidic solution comprises sulphuric acid.

6. The method of claim 1, comprising charging the adsorbent sites on the ion exchange resin with an ammonium bicarbonate solution.

7. The method of claim 1, further comprising at least one wash step after at least one of steps (a), (b), and (c).

8. The method of claim 7, wherein the at least one wash step comprises washing the ion exchange resin with an aqueous solution.

* * * * *